United States Patent
Del Bono et al.

(10) Patent No.: US 11,458,160 B2
(45) Date of Patent: Oct. 4, 2022

(54) FOOD SUPPLEMENTS FOR USE IN THE PROPHYLAXIS AND TREATMENT OF MIGRAINE

(71) Applicant: CRISTALFARMA S.R.L., Milan (IT)

(72) Inventors: Maria Cristina Del Bono, Milan (IT); Francesco Bonomo, Milan (IT)

(73) Assignee: CRISTALFARMA S.R.L., Milan (IT)

( * ) Notice: Subject to any disclaimer, the term of this patent is extended or adjusted under 35 U.S.C. 154(b) by 117 days.

(21) Appl. No.: 16/633,280

(22) PCT Filed: Jul. 23, 2018

(86) PCT No.: PCT/IB2018/055454
§ 371 (c)(1),
(2) Date: Jan. 23, 2020

(87) PCT Pub. No.: WO2019/021148
PCT Pub. Date: Jan. 31, 2019

(65) Prior Publication Data
US 2020/0147130 A1  May 14, 2020

(30) Foreign Application Priority Data
Jul. 26, 2017 (IT) .................. 102017000085185

(51) Int. Cl.
| | |
|---|---|
| *A61K 33/08* | (2006.01) |
| *A23L 33/105* | (2016.01) |
| *A23L 33/16* | (2016.01) |
| *A61K 31/365* | (2006.01) |
| *A61K 31/7034* | (2006.01) |
| *A61K 36/28* | (2006.01) |
| *A61K 36/76* | (2006.01) |

(52) U.S. Cl.
CPC ............ *A61K 33/08* (2013.01); *A23L 33/105* (2016.08); *A23L 33/16* (2016.08); *A61K 31/365* (2013.01); *A61K 31/7034* (2013.01); *A61K 36/28* (2013.01); *A61K 36/76* (2013.01); *A23V 2002/00* (2013.01)

(58) Field of Classification Search
CPC ....................................................... A61K 33/08
See application file for complete search history.

(56) References Cited

U.S. PATENT DOCUMENTS

| | | |
|---|---|---|
| 6,254,899 B1 | 7/2001 | Shrivastava |
| 6,500,450 B1 | 12/2002 | Hendrix |
| 2005/0036952 A1 | 2/2005 | Brucker |
| 2006/0233892 A1 | 10/2006 | Hendrix |
| 2014/0105878 A1 | 4/2014 | Kelleher |
| 2015/0238524 A1 | 8/2015 | Greene |

OTHER PUBLICATIONS

Herbal Products (Herbal Products, Toxicology and Clinical Pharmacology, 2nd edition, 2007, chapter 7). (Year: 2007).*
Pfaffenrath et al (Cephalalgia 1996, 16:436-40). (Year: 1996).*
Anonymous "Migraway for long term migraine & tension headache relief" Elixir Naturals, Jan. 1, 2016, URL http://www.elixirnaturals.com/product/migraway-for-long-term-migraine-tension-headache-relief.
Committee on Herbal Medicinal Products (HMPC): Assessment report on *Tanacetum parthenium* (L.) Schulz Bip., herba, European Medicine Agency Nov. 25, 2010.
Search Report and Written Opinion of PCT/IB2018/055454 dated Sep. 26, 2018.
Tepper Deborah, "Magnesium", Headache, vol. 53, No. 9, Oct. 1, 2013, pp. 1533-1534.

* cited by examiner

*Primary Examiner* — Benjamin J Packard
(74) *Attorney, Agent, or Firm* — Silvia Salvadori, P.C.; Silvia Salvadori

(57) ABSTRACT

Association of dry extract of feverfew, dry extract of willow and magnesium for use as an adjuvant in the prophylaxis and treatment of migraine and related oral compositions, in particular as a food supplement.

10 Claims, No Drawings

FOOD SUPPLEMENTS FOR USE IN THE PROPHYLAXIS AND TREATMENT OF MIGRAINE

This application is a U.S. national stage of PCT/IB2018/055454 filed 23 Jul. 2018, which claims priority to and the benefit of Italian Application No. 102017000085185 filed on 26 Jul. 2017, the contents of which are incorporated herein by reference in their entireties.

FIELD OF THE INVENTION

The present invention relates to the association of feverfew dry extract, willow dry extract and magnesium for use as an adjuvant in the prophylaxis and treatment of migraine and related oral compositions, in particular as a food supplement.

PRIOR ART 217 distinct forms of headaches have been catalogued.

However, according to the most up-to-date international classification[1], headaches have been re-catalogued according to different diagnostic levels, since it is important for the general practitioner to know at least the first and the second diagnostic levels of the classification.

The first level lists 14 groups: groups 1-4 concern primary headaches, groups 5-12 concern secondary headaches or headaches whose cause of pain is due to a specific pathology, group 13 is formed by cranial neuralgia and central facial pains and, finally, group 14 includes non-classifiable forms of headaches and neuralgia.

Primary headaches with greater prevalence of interest in general practice are migraine without aura, migraine with aura, childhood episodic syndromes that are possible migraine precursors, such as cyclic vomiting and abdominal migraine, paroxysmal vertigo; chronic migraine, cluster headache and tension headache.

Migraine with and without aura is a very common primary headache in Italy that has a high prevalence and a significant socio-economic impact in today's society.

Migraine without aura generally begins in adolescence or in early adulthood, but can also arise in childhood. However, an onset at 40-50 years of age is unlikely. It is a recurrent headache, in which a familiarity is often frequent.

During attacks, migraine sufferers tend to stay in bed, preferably in the dark and instinctively try to compress and cool the painful part.

The factors that most often trigger migraine without aura are psychological factors, routine changes, dietary factors, environmental factors, chemicals, work environment and hormonal factors.

With regard to this latter type of factors, monthly physiological hormonal fluctuations of female reproductive age deserve a specific mention. Therefore, the attacks more easily occur on perimenstrual days and on the day of ovulation.

Migraine with aura instead affects about 3-5% of the general population with a female-male ratio of 2:1. In almost 90% of cases, it begins within the age of 30. The distinctive element is the aura that generally precedes the headache and consists of a series of neurological symptoms due to focal encephalic dysfunction. These are visual, sensory, motor, retinal symptoms, alteration of speech and language and symptoms of encephalic brain dysfunction.

Chronic migraine, on the other hand, is due to a chronification of migraine without aura.

Arterial hypertension and depression are two conditions that contribute to the chronification of headache. In most cases, headaches are due to overuse of drugs such as NSAIDs, analgesics, ergotaminics, triptans, opioids, or associations thereof.

Daily or almost daily use for several months in a row of some drugs used to stop migraine attacks can trigger a vicious circle, thus leading to a continuous headache.

The tension headache is undoubtedly the most common headache found in the general population. All age groups can be affected, with a male-female ratio of 1:2. Psychological and physical factors seem to play an important role and an accumulation of psychophysical tension is generally present.

Cluster headache takes its name from the particular mode of recurrence of the attacks, which are grouped in delimited time periods. This type of headache affects 2-3 people in a thousand and, contrary to the previous ones, affects the male population more than the female.

A distinctive feature is the behaviour of the patient during the acute phase. Contrary to the migraine, the patient affected by cluster headache does not remain in a fixed position, is in continuous movement and is agitated and irritable.

In clinical practice, primary headaches including migraine with its variants and tension headaches are the most frequent and, as previously stated, affect mostly the female population.

They are triggered by a complex neurobiological phenomenon, caused by transient alterations of the functionality of nerve cells with no gross alterations of the nervous system. The neurophysiological bases of migraine are scarcely known today. In any case, neurotransmitters such as serotonin and neuronal membrane proteins are involved, such as the so-called sodium and potassium pump and other ion channels of the cell membrane. Moreover, especially for the tension headache, as stated above, irritability, anxiety states and depressive states contribute to their chronification.

It is now well established that migraine also involves a disturbance of the functionality of the vascular endothelium. The succession of migraine attacks with the consequent repetition of vasodilatative and oxidative phenomena can damage the endothelium functionality, thus causing an increase in its ability to produce vasoconstrictive substances at the expense of vasodilators.

Therefore, a migraine treatment should act on various factors, such as rebalancing the levels of serotonin, reducing oxidative inflammatory stress and stabilizing the cerebral electrical system.

Since, as previously stated, treatments of acute migraine phases with drugs such as NSAIDs can even lead to the chronification of the disease and, in any case, cannot be used at a prophylactic level, researchers have verified the effectiveness of alternative remedies, such as e.g. phytocomplexes.

The first and the most used for this type of pathology is the so-called feverfew, because it reduces the vasodilatation of the arterioles, favours the nociceptive reduction of the trigeminal and reduces the main cerebral proinflammatory cytokines (IL6, TNF-α, NF-kB) [2, 3, 4, 5].

Feverfew extract consists of whole or fragmented dried aerial parts of the plant *Tanacetum parthenium* and contains not less than 0.2% of parthenolide, namely the predominant sesquiterpene characterized by the following formula, wherein R=H

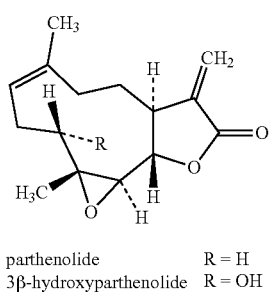

parthenolide R = H
3β-hydroxyparthenolide R = OH

Many clinical studies have evaluated the clinical efficacy of feverfew. These clinical studies show a certain reduction in the number of migraine attacks compared to placebo if feverfew is administered 3 times a day in the form of capsules containing 6.25 mg, with a parthenolide content for each formulation equal to 0.5 mg (about 8% of the weight of feverfew extract) [2].

However, the most recent studies conducted on a larger number of patients with respect to the previous ones gave non-convincing results if compared to placebo regarding a preventive activity on migraine of this phytocomplex [2].

The white willow dry extract (Salix alba) shows a general anti-inflammatory action, typical of salicylic derivatives. For these properties, this phytocomplex is used as antineuralgic and antipyretic drug, useful in case of rheumatism, joint and muscle pain, back pain, neuralgia, excellent against headaches [2, 6, 7, 8].

This phytocomplex with a titration ≥1.5%, administered on 10 patients in amounts of 300 mg together with 300 mg of feverfew with a titration ≥0.2%, administered twice a day for 12 weeks, resulted in a reduction of:

the frequency of migraine attacks (primary efficacy criterion) of 57.2% at 6 weeks ($p<0.029$) and of 61.7% at 12 weeks ($p<0.025$) in 9 out of 10 patients, with 70% of patients showing a 50% reduction of these attacks in 10/10 patients, the intensity of the attacks of 38.7% at 6 weeks ($p<0.005$) and 62.6% in 10/10 patients, with 70% of patients showing a reduction of intensity of at least 50%, the duration of the attacks (secondary efficacy criterion) of 67.2% at 6 weeks ($p<0.001$ and 76.2% at 12 weeks ($p<0.001$) in 10/10 patients [2, 6].

In spite of its remarkable results, this is still an open preliminary study that needs confirmation with a double-blind study, conducted on a decidedly higher number of patients [2].

In any case, to have a good efficacy, besides reducing relapses and pain control in the acute phases, a good medicament for migraine treatment and prophylaxis also needs to exert a greater control over the causes of migraine, which can for example be cerebral stress and anxiety states.

Magnesium has a muscle relaxant and anxiolytic activity. The lack of this mineral causes neuronal hyper excitability, thus playing an important role in the pathogenesis of the migraine attack. Indeed, it has been shown that the serum and intracellular magnesium levels are significantly reduced in subjects with migraine, [9, 10].

For example, it has been shown by a clinical study conducted on 81 patients aged 18-65 years with migraine classified according to the IHS (International Headache Society) criteria, who were orally given 600 mg of magnesium per day under the tri-magnesium di-citrate form for 12 weeks, or placebo. In the weeks 9-12 the attack frequency was reduced by 41.6% in the magnesium treated group and by 15.8% in the placebo group if compared to the baseline ($p<0.05$) [11].

For the acute treatment of migraine, 1000 mg of magnesium sulphate (corresponding to about 200 mg of magnesium) administered intravenously have shown a statistical improvement of all symptoms of migraine with aura or as an adjuvant in the treatment of migraine without aura. According to recent studies, the same amount of intravenous magnesium sulphate administered as a fast-acting drug is as effective as an association of dexamethasone and metoclopramide for the treatment of acute migraine [10, 11]. A further clinical study shows that intravenously administered magnesium sulphate in the same amounts of the previous studies is as effective as an intravenously administered NSAID such as ketorolac [12].

However, a clinical study shows that orally administered magnesium in amounts of the order of 300 mg and associated with 100 mg of feverfew and 400 mg of riboflavin is less effective in the treatment of migraine with riboflavin alone administered at even 16 times lower dosages (25 mg) [2].

SUMMARY OF THE INVENTION

The applicant has now found that the association of dry extract of feverfew, dry extract of white willow and magnesium is effective as an adjuvant in the treatment and prevention of primary headaches, such as, in particular, migraine with aura and without aura, tension and chronic headache, cluster headache, since besides reducing relapses and pain control in the acute phases, it also reduces cerebral stress and anxiety.

A further object of the present invention is an oral composition comprising the aforesaid association together with suitable excipients and/or diluents.

A further object of the present invention is a supplement comprising or even better consisting of the aforesaid oral composition.

DETAILED DESCRIPTION OF THE PRESENT INVENTION

For the purposes of the present invention, the expression "comprising/containing one or more components" does not exclude the presence of further components besides the one or more explicitly listed. For the purposes of the present invention, the expression in which an object "is made up or formed or composed of one or more components" means that the presence of further components in the object besides the one or more listed components is excluded.

Preferably, the above-mentioned association for use according to the present invention is orally administered.

The dry extract of feverfew in the association for use according to the present invention is preferably from the blossomed aerial parts of this plant and preferably has a parthenolide titration of at least 0.5%, and not more than 10%.

The dry extract of white willow comes preferably from the cortex of this plant and has a content in salicylic derivatives, and in particular in salicin, characterized by the following formula:

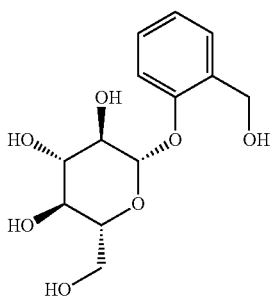

preferably not lower than 15% by weight based on the weight of the dry extract and preferably not higher than 30%. In any case, the amount of the dose of white willow extract to be administered for use according to the present invention must not exceed the maximum daily dose of salicin of 96 mg, as per Ministerial Regulations for Food Supplements.

Preferably, oxide or a pharmaceutically acceptable salt is used as the source of magnesium. Magnesium oxide is even more preferably used. Magnesium oxide, in fact, makes up 60% of the total weight of this compound, unlike pharmaceutically acceptable magnesium salts such as magnesium carbonate or citrate, containing only 24% and 14% of this element.

The oral compositions object of the present invention can be in the form of tablets, hard or soft capsules, powders or granules in the form of single-serving sachets, dispersible in water.

They are preferably in the form of tablets and contain:

feverfew with the aforesaid titration in amounts preferably ranging from 100 to 170 mg, more preferably 140 mg, white willow extract with the aforesaid salicin titration in amounts ranging from 300 to 350 mg, more preferably 320 mg, and magnesium in amounts ranging from 200 to 250 mg, more preferably 225 mg.

Preferably, the food supplement consists of said tablets, which are administered twice a day. In any case, the daily salicin amount must not exceed the aforementioned maximum permitted amount of 96 mg, and must not exceed the maximum permitted daily amount of magnesium of 450 mg, as per Ministerial Regulations for Food Supplements.

For the purposes of the present invention, food or dietary supplements correspond to the definition given in Article 2 of the Legislative Decree No. 169 of 21 May 2004, i.e. food products intended to supplement the common diet and constituting a concentrated source of nutrients, such as vitamins and minerals, or of other substances having a nutritional or physiological effect, in particular, but not exclusively, amino acids, essential fatty acids, fibres and extracts of plant origin, alone or in combination, in pre-dosed forms.

The following is a particularly preferred form of composition for food supplement in the form of tablets, in which the excipients and their contents are not reported.

The excipients involved in the preparation of this particularly preferred embodiment of food supplement according to the present invention are conventional excipients for the preparation of compressible powders, for example those mentioned in Remington the Science and Practice of Pharmacy 21st Edition.

Example 1—Food Supplement Formula for 1.2 g Tablets Administrable Twice a Day

| Components | Doses for a 1.2 g tablet |
|---|---|
| Feverfew - blossomed aerial parts dry extract | 140 mg |
| Parthenolides - minimum content: 0.5% | Min. 0.7 mg |
| White willow- cortex dry extract | 320 mg |
| Salicylic derivatives as salicin - minimum content 15% | 48 mg |
| Magnesium oxide | 373 mg |
| Magnesium content (60%) | 225 mg (60% of VNR*) (50% of the maximum permitted daily amount) |

*VNR: nutritional value of reference

BIBLIOGRAPHIC REFERENCES

1. Iurato L.—"Cefalee: nuova classificazione, criteri clinici e diagnostici per il medico di medicina generale". Clinical Management Issue 2014; 8(3):67-74.

2. "Assessment Report on Tanacetum parthenium (L.) Schulz Bip., Committee on Herbal Medicinal Product (HPMC). EMA/HMPC/587579/2009, 3. Pareek A. et al—"Feverfew (Tanacetum parthenium L.): A systematic review". Pharmacogn. Rev.2011; 5(9): 103-110.

4. Johnson E. S. et al—"Efficacy of feverfew as prophylactic treatment of migraine."British Medical Journal 1985; 291: 569-573;

5. Materazzi S. et al—"Parthenolide inhibits nociception and neurogenic vaso dilation in the trigemino vascular system by targeting TRPA1 channel" Pain 2013,154 (12): 2750-2758.

6. Shrivastava R. et al—"Tanacetum parthenium and Salix alba (Mig RL) association in migraine prophylaxis: a prospective, open label study" Clin. Drug Investig. 2006; 26(5): 287-296.

7. Flebich B. L. et al—"Effects of an ethanolic extract Salix extract on the release of selected inflammatory mediators in vitro" Phytomedicine 2004; 11 (2-3): 135-138.

8. Khayyal M. T. et al—Mechanisms involved in the anti-inflammatory effect of a standardized willow bark extract" Arzneimittelforschung2005; 55 (11): 677-687.

9. Assarzadegan F. et al—"Serum concentration of magnesium as an independent risk factor in migraine attacks: a matched case—control study and review of literature" Int. Clin. Psychpharmacol. 2016; 31(5): 287-292.

10. Pourshoghi A. et al—"Cerebral reactivity in migraine patients measured with functional near infrared spectroscopy" Eur. J. Med. Res. 2015; 20:96.

11. Gröber U. et al—"Magnesium in Prevention and Therapy" Nutrients 2015,7, 8199-8226.

12. Shahrami A. et al—"Comparison of therapeutic effects of magnesium sulfate vs. dexamethasone/metoclopramide on alleviating acute migraine headache" J. Emerg. Med. 2015; 48(1): 69-76.

13. Kasmaei H. D. et al "ketorolac cersus Magnesium Sulfate in Migraine headache Pain Management; a Preliminary Study" Emergency 2017; 5(1):1-4.

The invention claimed is:

1. A method for treating and preventing feverfew primary headaches comprising orally administering, as adjuvant to a subject in need thereof, a therapeutically effective amount of:
feverfew dry extract,
white willow dry extract and
magnesium.

2. The method of claim 1, wherein said primary headaches are migraine with and without aura, tension headache, chronic headache and cluster headache.

3. The method of claim 1, wherein said feverfew dry extract comes from the blossomed part of said plant and has a parthenolide content not lower than 0.5% and not higher than 10% by weight of the overall weight of said extract.

4. The method of claim according to claim 1, wherein said dry white willow extract comes from the cortex of said plant and has a salicin content not lower than 15% and not higher than 30% by weight of the overall weight of said extract.

5. The method of claim 1, wherein said magnesium source is Magnesium oxide containing magnesium in amounts of 60% by weight on the weight of said oxide.

6. The method of claim 1, wherein said feverfew dry extract, white willow dry extract, and magnesium are administered in the form of and oral composition containing them, as active ingredients in combination with suitable excipients and/or diluents.

7. The method of claim 6, wherein said oral composition said feverfew extract comes from the blossomed aerial part of said plant and has a parthenolide content not lower than 0.5% and not higher than 10% by weight of the overall weight of said extract, said white willow dry extract comes from the cortex of said plant and has a salicin content not lower than 15% and not higher than al 30% by weight of the overall weight of said extract, said magnesium source is magnesium oxide which contains 60% by weight of magnesium of the weight of said oxide,
provided that
i) the amount of salicin does not exceed the maximum recommended daily dose of 96 mg;
ii) the amount of magnesium does not exceed the maximum recommended daily dose of 450 mg.

8. The method of claim 6, wherein said oral composition is in the form of a tablet administrable twice a day including:
feverfew in amounts between 100 and 170 mg,
white willow extract in amounts between 300 and 350 mg
magnesium in amount between 200 and 250 mg.

9. The method of claim 8, containing 140 mg of feverfew dry extract, 320 mg of white willow dry extract and 225 mg of magnesium.

10. The method of claim 6, wherein said oral composition is a dietary supplement.

* * * * *